(12) United States Patent
Wiemker et al.

(10) Patent No.: US 11,042,987 B2
(45) Date of Patent: Jun. 22, 2021

(54) DEVICE AND METHOD FOR MODELLING A COMPOSITION OF AN OBJECT OF INTEREST

(71) Applicant: KONINKLIJKE PHILIPS N.V., Eindhoven (NL)

(72) Inventors: Rafael Wiemker, Kisdorf (DE); Tobias Klinder, Uelzen (DE); Heike Ruppertshofen, Ahrensburg (DE); Nicole Schadewaldt, Norderstedt (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/606,249

(22) PCT Filed: Apr. 18, 2018

(86) PCT No.: PCT/EP2018/059904
§ 371 (c)(1),
(2) Date: Oct. 18, 2019

(87) PCT Pub. No.: WO2018/192971
PCT Pub. Date: Oct. 25, 2018

(65) Prior Publication Data
US 2020/0043173 A1 Feb. 6, 2020

(30) Foreign Application Priority Data
Apr. 18, 2017 (EP) .................................. 17166802

(51) Int. Cl.
*G06K 9/00* (2006.01)
*G06T 7/12* (2017.01)
(Continued)

(52) U.S. Cl.
CPC ............... *G06T 7/12* (2017.01); *A61B 6/032* (2013.01); *G06K 9/6202* (2013.01); *G06K 2209/05* (2013.01); *G06T 2207/10081* (2013.01)

(58) Field of Classification Search
CPC ...... G06K 9/6202; G06K 9/48; G06K 9/4609; G06K 2209/05; G06T 7/12; G06T 7/0012;
(Continued)

(56) References Cited

U.S. PATENT DOCUMENTS

| 5,023,895 A | * | 6/1991 | McCroskey | ......... G01N 23/046 378/10 |
| 6,278,761 B1 | * | 8/2001 | Kim | ...................... G06T 7/0012 378/8 |

(Continued)

OTHER PUBLICATIONS

PCT International Search Report, International application No. PCT/EP2018/059904, dated Jul. 25, 2018.
(Continued)

*Primary Examiner* — Amir Alavi
(74) *Attorney, Agent, or Firm* — Larry Liberchuk

(57) ABSTRACT

A method for modelling a composition of an object of interest comprises segmenting object of interest image data provided by computer tomography image data resulting in a plurality of image segments. A determined Hounsfield density value is then extracted from the object of interest image data for each image segment. A component ratio of at least two component classes is defined for the object of interest, the at least two component classes having different component Hounsfield density values. At least one component class is assigned to each image segment based on the corresponding determined Hounsfield density value resulting in simulated image segments comprising the component Hounsfield density values. The simulated image segments
(Continued)

define simulated image data of the object of interest, where a ratio of the assigned component classes corresponds to the component ratio. A deviation between the simulated image data and the object of interest image data is then determined.

12 Claims, 5 Drawing Sheets

(51) Int. Cl.
 *A61B 6/03* (2006.01)
 *G06K 9/62* (2006.01)
(58) Field of Classification Search
 CPC ... G06T 7/0081; G06T 7/0083; G06T 11/003; G06T 2207/10081; G06T 2207/10016; G06T 2207/20144
 See application file for complete search history.

(56) References Cited

U.S. PATENT DOCUMENTS

| | | | | |
|---|---|---|---|---|
| 6,824,759 | B2* | 11/2004 | Thakur | A61K 51/088 424/1.11 |
| 7,496,217 | B2* | 2/2009 | Tank | G06K 9/00201 382/128 |
| 8,164,335 | B2* | 4/2012 | Huwer | G01R 33/4833 324/309 |
| 8,705,827 | B2* | 4/2014 | Zhu | G06T 5/50 382/131 |
| 8,705,830 | B2* | 4/2014 | Ringl | G06T 19/00 382/131 |
| 9,119,590 | B2* | 9/2015 | Budoff | A61B 6/505 |
| 9,142,018 | B2* | 9/2015 | Robert | A61B 34/20 |
| 9,691,168 | B2* | 6/2017 | Song | G06T 11/006 |
| 10,176,568 | B2* | 1/2019 | Jung | A61B 6/583 |
| 2009/0252395 | A1 | 10/2009 | Chan | |
| 2014/0180061 | A1 | 6/2014 | Warntjes | |
| 2020/0043173 | A1* | 2/2020 | Wiemker | G06K 9/6223 |

OTHER PUBLICATIONS

McWilliams A. et al., "Probability of Cancer in Pulmonary Nodules Detected on First Screening CT", N Engl J Med. Sep. 5, 2013; 369(10).

Ciompi F. et al., "Towards Automatic Pulmonary Nodule Management in Lung Cancer Screening with Deep Learning", Scientific Reports, vol. 7, No. 46479, pp. 1-9, Apr. 2017.

Levesque I.R. et al., "Characterizing Healthy and Diseased White Matter using Quantitative Magnetization Transfer and Multicomponent T2 Relaxometry: A Unified View Via a Four-Pool Model", Magnetic Resonance in Medicine, Dec. 2009; vol. 62, Issue 6, pp. 1487-1496.

Farag A.A. et al., "Data-Driven Lung Nodule Models for Robust Nodule Detection in Chest CT", ICPR '10 Proceedings of the 2010 20th International Conference on Pattern Recognition, ICPR 2010, Istanbul, Turkey, pp. 2588-2591, Aug. 23-26, 2010.

Pousse A. et al., "Pulmonary Nodule Distribution Modeling as a Diagnostic Tool for HRCT Image Analysis", IEEE Transactions on Nuclear Science, vol. 51, No. 3, pp. 690-695, Jun. 2004.

Yushkevich P A et al: "User-Guided 3D Active Contour Segmentation of Anatomical Structures: Significantly Improved Efficiency and Reliability", Neuroimage, Elsevier, Amsterdam, NL, vol. 31, No. 3, Jul. 1, 2006 (Jul. 1, 2006), pp. 1116-1128.

S. Hu et al: "Automatic Lung Segmentation for Accurate Quantitation of Volumetric X-Ray CT Images", IEEE Transactions on Medical Imaging., vol. 20, No. 6, Jun. 1, 2001 (Jun. 1, 2001), pp. 490-498.

Alexandra Derntl et al: "Clustering Techniques for Neuroimaging Applications Clustering Techniques in Neuroimaging", Wiley Interdisciplinary Reviews: Data Mining and Knowledge Discovery, vol. 6, No. 1, Dec. 22, 2015 (Dec. 22, 2015), pp. 22-36.

Levesque I.R. et al., "Quantitative Magnetic Resonance Imaging of Magnetization Transfer and T2 Relaxation in Human White Matter Pathology", Department of Physics and Medical Physics Unit, Oct. 2009.

* cited by examiner

DEVICE AND METHOD FOR MODELLING A COMPOSITION OF AN OBJECT OF INTEREST

FIELD OF THE INVENTION

The present invention relates to a device and a system for modelling a composition of an object of interest and a method for modelling a composition of an object of interest.

BACKGROUND OF THE INVENTION

Lung cancer is one of the most dangerous cancer types having a high mortality. Lung tumors may be detected with several methods. One of those methods is computed tomography imaging of the patient's lung.

Lung cancer screening with computer tomography imaging is recognized as mortality reducing. In most cases, big tumors are clearly shown in the computer tomography image whereas very small tumors, so called nodules, are depicted on just a few pixels.

However, even in high risk groups, only 1 in 20 lung nodules is cancerous. It has therefore to be assessed whether a nodule is malignant or benign. An important descriptor to assess the risk whether a nodule is malignant or benign, is the tissue type of the nodule. The nodule tissue type describes the tissue composition, and is often categorized into four classes: calcified, solid, mixed, and ground-glass. The latter two types also known as part-solid and sub-solid. The nodule type is also a descriptor of the Lung Reactive Airways Dysfunction Syndrome (RADS) reporting scheme required for screening reimbursement.

Each of the four nodule types is a super-class which comprises a multitude of different tissue compositions consisting of calcified, solid, and sub-solid tissue. Moreover, each type may have many different sizes and shapes. Furthermore, the typical Hounsfield densities of these tissue types, may not even be present in the histogram of the nodule because small areas of high densities are prone to dilution, i.e. blurring due to the partial volume effect of the imaging point spread function.

It is known to perform an automatic classification of the nodule type. Those automatic classification methods of the nodule type for a given new nodule in question are performed by training a classifier on a database of manually classified samples. The database must be large enough to cover the wide range of different compositions, shapes, and sizes. However, such a comprehensive and balanced database is very costly and time consuming to establish, and it might be biased towards certain nodule types, depending on the balances of types within the training data base.

For magnetic resonance imaging simulations for determining a tissue composition are known. For example, in US 2014/0180061 A1 a map of the myelin tissue of the brain is generated. The composition of the myelin tissue is assumed to have at least two components. Then an initial ratio of the components is fitted to the measurement. However, this method needs a high amount of computer power to be performed in an adequate time.

SUMMARY OF THE INVENTION

There may thus be a need to provide a method and a device performing a low cost, fast and non-biased automatic classification of a tumor composition.

The object of the present invention is solved by the subject-matter of the independent claims; further embodiments are incorporated in the dependent claims. It should be noted that the following described aspects of the invention apply also for the system and the method.

According to an aspect, a device for modelling a composition of an object of interest comprises: a processing unit; wherein the processing unit comprises: an image data segmenter; an extraction module; a definition module; an assigning module; and a comparator; wherein the image data segmenter is configured to segment the object of interest image data provided by computer tomography image data into image segments; wherein the extraction module is configured to extract a Hounsfield density value from the image segments; wherein the definition module is configured to define a component ratio of at least two component classes for the object of interest, the at least two component classes having different component Hounsfield density values; wherein the assigning module is configured to assign at least one component class to each image segment based on the corresponding determined Hounsfield density value resulting in simulated image segments comprising the component Hounsfield density values, the simulated image segments defining simulated image data of the object of interest; wherein a ratio of the assigned component classes corresponds to the component ratio; wherein the comparator is configured to determine a deviation between the simulated image data and the object of interest image data; and wherein the processing unit is configured to vary the component ratio being defined by the definition module until the deviation corresponds to a predefined minimum deviation resulting in a final component ratio.

The device provides a simulation of the determined computer tomography image data from the object of interest, which e.g. may be a tumor. The image data provided is first segmented into image segments. The Hounsfield density value being determined by the computer tomography is extracted from those image segments. The simulation provided by the device simulates the object of interest by assuming a composition of component classes having component Hounsfield density values. Those component Hounsfield density values are assumed values for the component classes of the assumed composition. By using the component Hounsfield density values and the assumed composition, the device determines a simulated image of the object of interest.

The assumed composition comprises at least two assumed different component classes each having an assumed different Hounsfield density value. The assumption further refers to the component ratio between the at least two different component classes.

This means, that the simulated object of interest is assumed to consist of components which are categorized in the component classes and which have a distribution in the simulated object of interest matching the component ratio of component classes. For simulating the component ratio of the object of interest, the component Hounsfield density values are assigned to the image segments. The assignment of the component Hounsfield density value is performed based on the determined Hounsfield density value of each image segment. For example, image segments having a high determined Hounsfield density value are assigned with a high component Hounsfield density value, whereas image segments having a low determined Hounsfield density value are assigned with a low component Hounsfield density value. The ratio between the image segments having a high component Hounsfield density value and the image segments having a low component Hounsfield density value matches the component ratio, i.e. is the simulated image segments have the same ratio as the component classes in the simulated object of interest.

The simulated object of interest resulting from that assignment then comprises image sections having different component Hounsfield density values. The comparator compares the simulated object of interest, i.e. the simulated image data comprising the component Hounsfield density values, to the determined object of interest, i.e. the object of interest image data comprising the determined Hounsfield density values. The deviation resulting from that comparison is then compared to a predefined minimum deviation.

If the deviation determined from the comparator is higher than the predefined minimum deviation the above described simulation of the object of interest is repeated with the amended assumed component ratio.

If the deviation determined from the comparator equals or is lower than the predefined minimum deviation the actual component ratio is defined to be the final component ratio.

The device provides a simulation of the components of an object of interest being a low cost, fast and non-biased automatic classification of a tissue composition. The device can simulate the object of interest without being dependent on a comprehensive database with clinical samples for training.

According to an example, the processing unit further comprises a sorting module; wherein the sorting module is configured to sort the image segments based on the determined Hounsfield density values resulting in a sorted list of image segments; and wherein the assigning module segments the sorted list into portions, the ratio between the portions being the component ratio and wherein the component classes are assigned to the portions of the sorted list in accordance with the component ratio.

The sorting of the image segments into a sorted list simplifies the assignment of the component Hounsfield density values to the image segments based on the determined Hounsfield density values. The sorted list of image segments is divided into several list segments which equal the number of component classes having an assumed non-zero portion in the simulated object of interest.

Thereby, the ratio between the component classes is used to determine the ratio between the list segments. For determining the ratio between the component classes, the component classes are sorted based on the component Hounsfield density value. This means, that the component class having the highest Hounsfield density value defines the ratio for the list segment having the highest mean determined Hounsfield density value. In accordance, the component class having the lowest component Hounsfield density value defines the ratio for the list segment having the lowest mean determined Hounsfield density value. The same applies for the component classes and the list segments between the component classes and list segments having the highest and lowest component Hounsfield density value and the mean determined Hounsfield density value, respectively.

Then, the component Hounsfield density value of the component class defining the ratio for the corresponding list segment is assigned to each image segment of that list segment. The result is a sorted list of image segments with a number of different component Hounsfield density values being significantly lower than the number of determined Hounsfield density values. That number may correspond to the number of component classes or may be lower than the number of component classes. The sorting of the image segments thus simplifies the finding of a result having a minimum deviation since the determined Hounsfield density values of the image segments are taken into account for the simulation. This means, that the highest component Hounsfield density value of the assumed composition ratio will be assigned to an image segment having the highest determined Hounsfield density value. Furthermore, the lowest component Hounsfield density value of the assumed composition ratio will be assigned to an image segment having the lowest determined Hounsfield density value. Thus, the simulation is performed within reasonable boundary conditions which further simplify the simulation of the object of interest and further increases the simulation speed.

In a further example, the processing unit further comprises: a folding module; wherein the folding module is configured to fold the simulated image data with a blurring function; and wherein the processing unit varies the blurring function when varying the component ratio.

Folding the simulated image data with a blurring function will provide a smaller deviation between the simulated image data and the determined image data of the object of interest. The folding simulates the effects of the image acquisition device, e.g. effects of the imaging point spread function. That effects may for example result from the optics of the image acquisition device or form of the detector of that image acquisition device. If the blurring function of the image acquisition device is known then that blurring function is used for the simulation of the object of interest image data.

In an example, the device further comprises: a display unit; wherein the processing unit is further configured to compare the final component ratio with a predefined object type list resulting in a determined object type of the object of interest; and wherein the display unit is configured to communicate the determined object type to a user.

In another example, the device further comprises: an output unit; wherein the object of interest is a tumor; and wherein the output unit is configured to transmit the determined object type into a tumor malignancy assessment scheme.

In an example, the image segments are voxels or pixels or a plurality of pixels.

According to a further aspect, a system for modelling a composition of an object of interest comprises: a computer tomography imaging device; and a device according to the above description; wherein the device comprises an input unit; wherein the input unit is configured to receive computer tomography image data; and wherein the computer tomography imaging device is configured to acquire and to transmit computer tomography image data.

According to an aspect, a method for modelling a composition of an object of interest comprises the following steps: a) segmenting object of interest image data provided by computer tomography image data resulting in a plurality of image segments; b) extracting a determined Hounsfield density value from the object of interest image data for each image segment; c) defining a component ratio of at least two component classes for the object of interest, the at least two component classes having different component Hounsfield density values; d) assigning at least one component class to each image segment based on the corresponding determined Hounsfield density value resulting in simulated image segments comprising the component Hounsfield density values, the simulated image segments defining simulated image data of the object of interest; wherein a ratio of the assigned component classes corresponds to the component ratio; e) determining a deviation between the simulated image data and the object of interest image data; and f) repeating steps c) to e) with varied component ratios until the deviation corresponds to a predefined minimum deviation resulting in a final component ratio.

The method provides a simulation of the determined computer tomography image data from the object of interest, which e.g. may be a tumor. The image data provided is first segmented into image segments. The Hounsfield density value being determined by the computer tomography is extracted from those image segments. The simulation provided by the method simulates the object of interest by assuming a composition of component classes having component Hounsfield density values. Those component Hounsfield density values are assumed values for the component classes of the assumed composition. By using the component Hounsfield density values and the assumed composition, the method determines a simulated image of the object of interest.

The assumed composition comprises at least two assumed different component classes each having an assumed different Hounsfield density value. The assumption further refers to the component ratio between the at least two different component classes.

This means, that the simulated object of interest is assumed to consist of components which are categorized in the component classes and which have a distribution in the simulated object of interest matching the component ratio of component classes. For simulating the component ratio of the object of interest, the component Hounsfield density values are assigned to the image segments. The assignment of the component Hounsfield density value is performed based on the determined Hounsfield density value of each image segment. For example, image segments having a high determined Hounsfield density value are assigned with a high component Hounsfield density value, whereas image segments having a low determined Hounsfield density value are assigned with a low component Hounsfield density value. The ratio between the image segments having a high component Hounsfield density value and the image segments having a low component Hounsfield density value matches the component ratio, i.e. is the simulated image segments have the same ratio as the component classes in the simulated object of interest.

The simulated object of interest resulting from that assignment then comprises image sections having different component Hounsfield density values. The comparing step compares the simulated object of interest, i.e. the simulated image data comprising the component Hounsfield density values, to the determined object of interest, i.e. the object of interest image data comprising the determined Hounsfield density values. The deviation resulting from that comparison is then compared to a predefined minimum deviation.

If the determined deviation is higher than the predefined minimum deviation the above described simulation of the object of interest is repeated with the amended assumed component ratio.

If the determined deviation equals or is lower than the predefined minimum deviation the actual component ratio is defined to be the final component ratio.

The method provides a simulation of the components of an object of interest being a low cost, fast and non-biased automatic classification of a tissue composition. The method can simulate the object of interest without being dependent on a comprehensive database with clinical samples for training.

In an example, prior to step c) the method comprises the following step: g) sorting the image segments based on the determined Hounsfield density values resulting in a sorted list of image segments; wherein in step d) the sorted list is segmented into portions, the ratio between the portions corresponding to the component ratio and wherein the component classes are assigned to the portions of the sorted list in accordance with the component ratio.

The sorting of the image segments into a sorted list simplifies the assignment of the component Hounsfield density values to the image segments based on the determined Hounsfield density values. The sorted list of image segments is divided into several list segments which equal the number of component classes having an assumed non-zero portion in the simulated object of interest.

Thereby, the ratio between the component classes is used to determine the ratio between the list segments. For determining the ratio between the component classes, the component classes are sorted based on the component Hounsfield density value. This means, that the component class having the highest Hounsfield density value defines the ratio for the list segment having the highest mean determined Hounsfield density value. In accordance, the component class having the lowest component Hounsfield density value defines the ratio for the list segment having the lowest mean determined Hounsfield density value. The same applies for the component classes and the list segments between the component classes and list segments having the highest and lowest component Hounsfield density value and the mean determined Hounsfield density value, respectively.

Then, the component Hounsfield density value of the component class defining the ratio for the corresponding list segment is assigned to each image segment of that list segment. The result is a sorted list of image segments with a number of different component Hounsfield density values being significantly lower than the number of determined Hounsfield density values. That number may correspond to the number of component classes or may be lower than the number of component classes. The sorting of the image segments thus simplifies the finding of a result having a minimum deviation since the determined Hounsfield density values of the image segments are taken into account for the simulation. This means, that the highest component Hounsfield density value of the assumed composition ratio will be assigned to an image segment having the highest determined Hounsfield density value. Furthermore, the lowest component Hounsfield density value of the assumed composition ratio will be assigned to an image segment having the lowest determined Hounsfield density value. Thus, the simulation is performed within reasonable boundary conditions which further simplify the simulation of the object of interest and further increases the simulation speed.

According to a further example, step d) comprises the following sub-step: d1) folding the simulated image data with a blurring function; and wherein in step f) the blurring function is varied when varying the component ratio.

Folding the simulated image data with a blurring function will provide a smaller deviation between the simulated image data and the determined image data of the object of interest. The folding simulates the effects of the image acquisition device, e.g. effects of the imaging point spread function. That effects may for example result from the optics of the image acquisition device or form of the detector of that image acquisition device. If the blurring function of the image acquisition device is known then that blurring function is used for the simulation of the object of interest image data.

In another example, the method further comprises the steps: h) comparing the final component ratio with a predefined object type list resulting in a determined object type of the object of interest; and i) communicating the determined object type to a user.

In a further example, the object of interest is a tumor; and wherein the method further comprises the steps: j) feeding the determined object type into a tumor malignancy assessment scheme.

According to a further aspect, a computer program element for controlling an apparatus according to the description mentioned above, which, when being executed by a processing unit, is adapted to perform the method steps of the method according to the above description.

In a further aspect, a computer readable medium has stored the program element mentioned above.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 3:
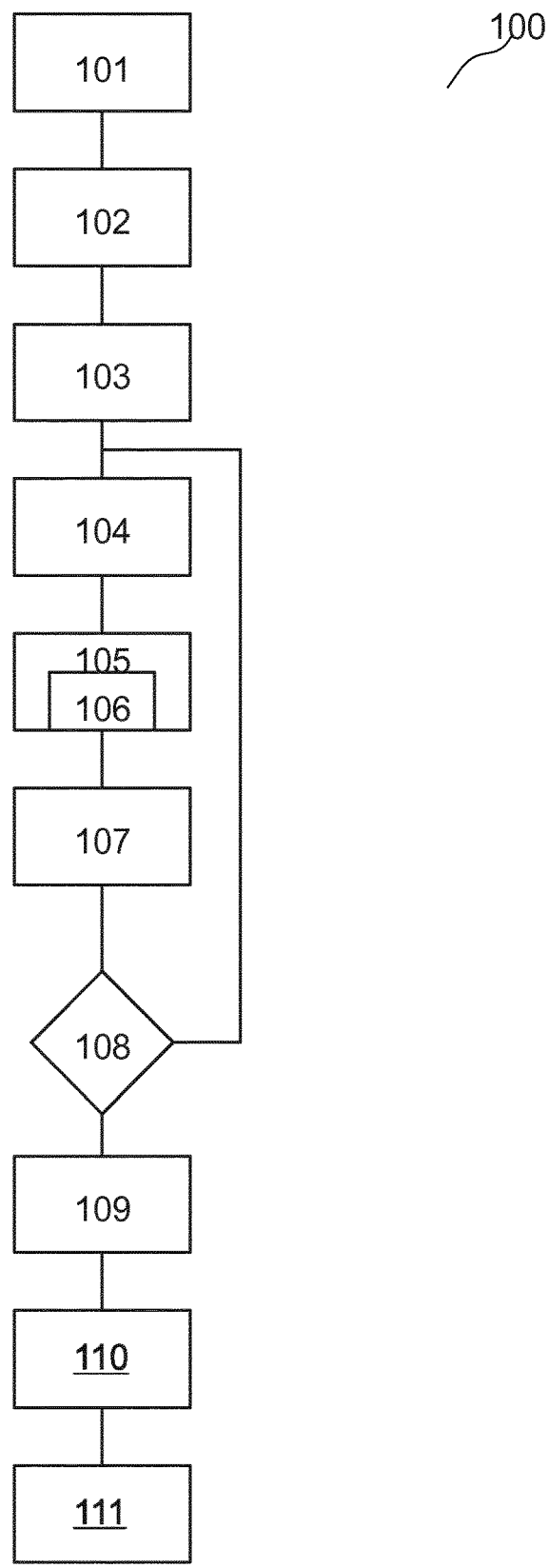
FIG. 3 shows a schematic flow chart of the method for modeling a composition of an object of interest.

Before further describing the imaging system and the device for modelling a composition of an object of interest, examples of a method for modelling a composition of an object of interest are described in further detail referring to FIG. 3.

FIG. 3 shows a flow chart representing an example of the method 100.

The method 100 uses computer tomography image data comprising an object of interest image data were in the object of interest image data depicts an object of interest 7.

The object of interest 7 may be a nodule being depicted by the object of interest image data in two dimensions or three dimensions.

The method 100 may comprise an object recognition step in which the object of interest image data is recognized in the computer tomography image data.

The object of interest image data is segmented 101 into a plurality of image segments 71-80. The image segments 71-80 may be voxels or pixels depicting portions of the object of interest 7. The segmentation may be represented by a label volume or by a surface mesh.

Then, the determined Hounsfield density value of each image segment 71-80 is extracted 102. The determined Hounsfield densities represent the absorption of the object of interest 7 being determined by the computer tomography calculation. The Hounsfield density value may be represented by a grayscale value of the object of interest image data.

Figure 6A:
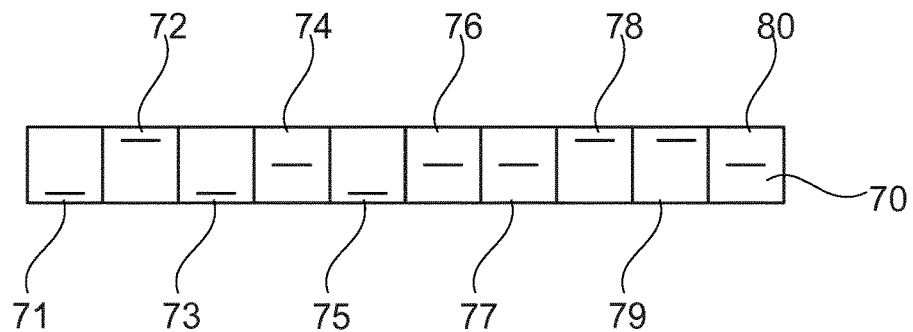
FIG. 6a-d show a schematic view of the sorting of the image segments and the assigning of the component Hounsfield density values.

FIG. 6a shows a schematic view of the image segments 71-80, wherein the horizontal lines in the squares represents the determined Hounsfield density values.

In the next step, the image segments 71-80 are sorted 103 based on the determined Hounsfield density value. This means a sorted list 81 is generated which comprises the image segments 71-80 wherein the determined Hounsfield density value of each image segment 71-80 determines the rank of the corresponding image segment 71-80 in the sorted list 81.

Figure 6B:
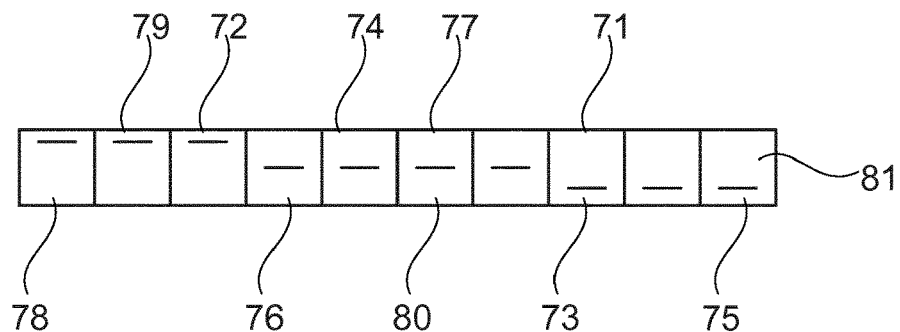

An example of a sorted list 81 is shown in FIG. 6b. If the sorted list 81 is for example a linear list having two end portions, one end portion comprises the image segments 71-80 having the highest determined Hounsfield density values whereas the other end portion comprises the image segments 71-80 having the lowest determined Hounsfield density values. The end portions define list segments having different mean determined Hounsfield density values.

Figure 6C:
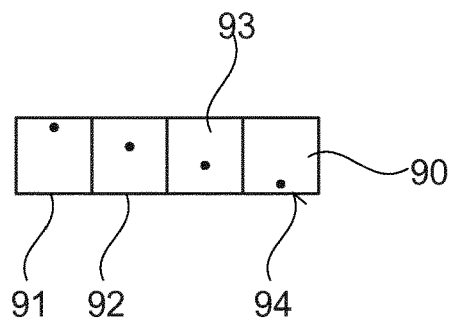

After sorting 103 the image segments 71-80, a component ratio of component classes 91 to 94 is defined for the object of interest 7. For example, it is assumed that the object of interest 7 comprises four component classes 91 to 94. If the object of interest 7 is a nodule the component class 91 may represent calcified tissue having an assumed calcified Hounsfield density value of 300 as component Hounsfield density value, the component class 92 may represent solid tissue having an assumed solid Hounsfield density value of 0 as component Hounsfield density value, the component class 93 may represent ground-glass tissue having an assumed ground-glass Hounsfield density value of −500 as component Hounsfield density value, and the component class 94 may represent parenchyma having an assumed parenchyma Hounsfield density value of −750 to −950 as component Hounsfield density value. FIG. 6c shows a schematic view of the component classes 91 to 94, wherein the dot in the squares symbolizes the determined Hounsfield density value.

The component ratio of the component classes 91 to 94 may be assumed to be 40%:20%:20%:20% as the ratio between component class 91 versus component class 92 versus component class 93 versus component class 94. The portions of the component classes 91 to 94 sum up to 100%.

Figure 6D:
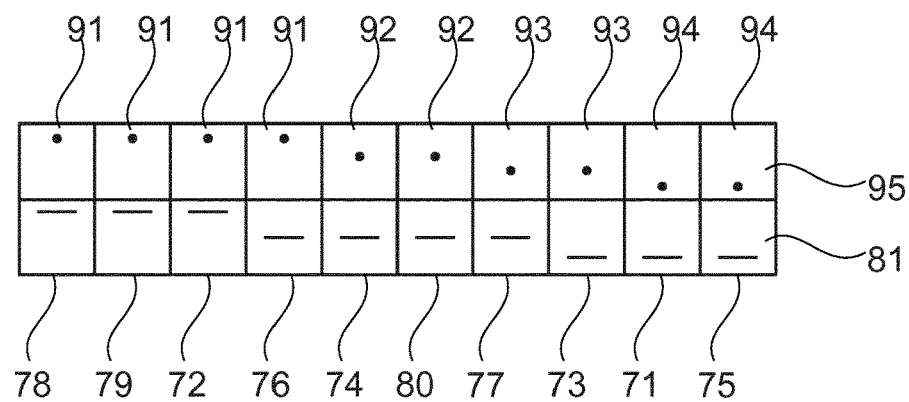

In the next step, at least one component class 91 to 94 is assigned 105 to each image segment 71-80 based on the determined Hounsfield density value from that image segment 71-80. Since in this example the image segments 71-80 are sorted in a sorted list 81, the first 40% of image segments 71-80 of the sorted list 81 are assigned the component Hounsfield density value of the component class 91, i.e. the component Hounsfield density value of 300. According to FIG. 6d, the first 40% of image segments 71-80 of the sorted list 81 are image segments 78, 79, 72, and 76 which are assigned to the component class 91. The rest of the image segments 71-80 is assigned accordingly, i.e. the following 20% of the sorted list 81, being image segments 74 and 80, are assigned to component class 92, the next 20% of the sorted list 81, being image segments 77 and 73, are assigned to component class 93, and the last 20% of the sorted list 81, being image segments 71 and 75, are assigned to the component class 94. The result is a list 95 of simulated image segments.

Simulated image data is created by generating simulated image segments being at the same position in the simulated image data as the image segments 71-80 in the object of interest image data. The simulated image segments comprise the respective component Hounsfield density values according to the assigning step 105.

Next, a blurring may be simulated by mathematically folding 106 a blurring function with the simulated image data. The blurring function may be a Gaussian having the width B. The blurring function may simulate the point distribution function of a computer tomography scanner.

In an alternative embodiment blurring may be simulated by mathematically folding 106 a known device blurring function with the simulated image data. The known device blurring function exactly simulates the blurring of a specific device being used for acquiring the computer tomography data.

Then, the deviation between the simulated image data and the object of interest image data is determined 107. A distance measure may be used to determine the deviation between the simulated image data and the object of interest image data. The distance measure may for example be the mean difference or a linear correlation.

The steps 104, 105, 106 and 107 are repeated 108 if the deviation is higher than a predefined minimum deviation, wherein the component ratio in step 104 is amended. The following iteration may therefore be performed with a component ratio of 35%:25%:20%:20%.

By only amending the component ratio, a big amount of computing time may be saved compared to known simulation methods. The optimization of the function of the component ratio and the blurring function can be performed using a standard-optimizer algorithm, or by exhaustive parallel search, as the required computation cost per trial is very small. After the amendment of the component ratio the assignment of the component Hounsfield density values follows a well-defined assignment scheme which may be performed in a short time. The method described above ensures that the determined Hounsfield density values of the image segments 71-80 are taken into account when trying to find the final composition ratio of the object of interest. Therefore, a randomly performed trial and error approach is prevented.

If in step 108 the deviation between the simulated image data and the object of interest image data corresponds to a predefined minimum deviation, i.e. if the deviation equals the predefined minimum deviation or is below the predefined minimum deviation, the component ratio of the last iteration is defined to be the final component ratio.

Before defining 104 a component ratio, a Hounsfield density value of the area surrounding the object of interest 7 may be determined as a peak of the Hounsfield histogram of the provided computer tomography image data in a certain neighborhood around the object of interest 7, e.g. around a 40 mm radius.

Further, for providing optimized comparisons conditions, all image data 9 outside the object of interest image data in the computer tomography image 8 data may be set to the parenchyma Hounsfield density value. The image data 9 outside of the object of interest image data is then uniform. Furthermore, the simulated tissue being outside the object of interest 7 in the simulated image data may also be set to the parenchyma Hounsfield density value such that the comparison only finds deviations between the simulated image data and the object of interest image data.

The final component ratio may be compared 109 with a predefined object type list. The predefined object type list may be a textbook-like rule to find an object type of the object of interest. The rules for determining the object type may e.g. be calcified if the final component ratio determines more than 50% for component class 91, solid if the final component ratio determines more than 50% for component class 92, mixed if the final component ratio determines more than 50% for component class 93 and more than 5% for component class 92, and ground-glass otherwise. In case, the object of interest is a nodule the final component ratio may determine what kind of nodule has been simulated.

The determined object type may be communicated 110 to a user. The user can then decide how to further use that result.

Furthermore, the determined object type may be fed 111 into a tumor malignancy assessment scheme. That assessment scheme may provide criteria which may provide boundaries for different tumor types and their malignancy potential. The outcome of the tumor malignancy assessment scheme may be provided to a user.

Figure 1:
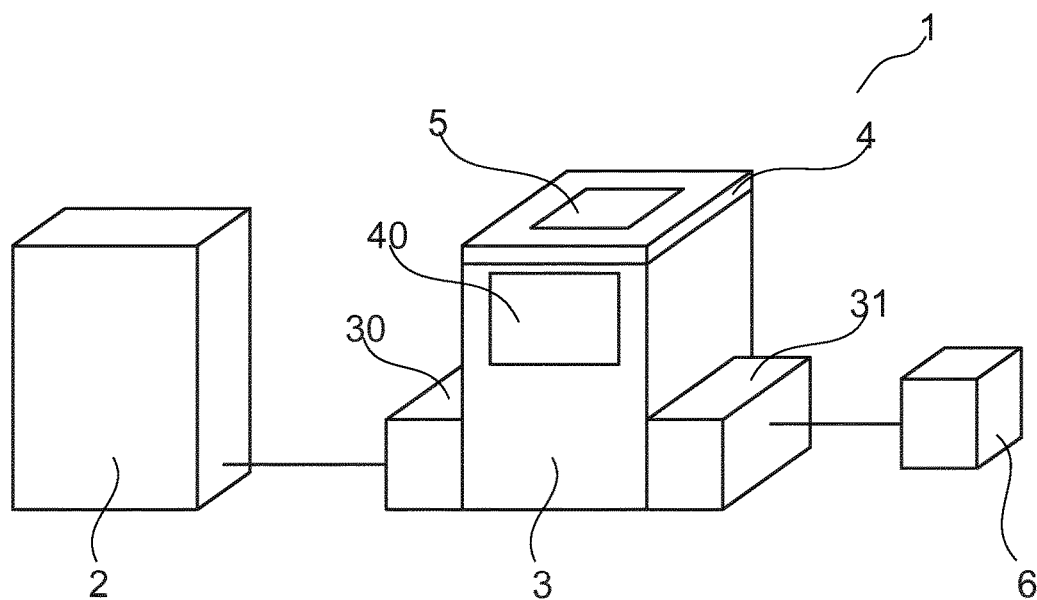
FIG. 1 shows a schematic view of the system for modeling a composition of an object of interest.

FIG. 1 shows a system 1 for modelling a composition of an object of interest 7. The system comprises a computer tomography imaging device 2, a device 3 for modelling a composition of an object of interest 7, and a tumor malignancy assessment scheme module 6.

The computer tomography imaging device 2 provides computer tomography imaging data of a patient's lung wherein the patient's lung may comprise a nodule which may be the object of interest 7. The computer tomography imaging device 2 may emit the computer tomography imaging data of the patient's lung.

The device 3 may comprise an input unit 30 which may receive computer tomography imaging data. For example, the input unit 30 may receive the computer tomography imaging data of the patient's lung being emitted by the computer tomography imaging device 2.

Furthermore, the device 3 may comprise an object recognition module (not shown) which is configured to recognize the object of interest image data in the computer tomography image data.

The device 3 may further perform the method being described above to determine an object type based on a final composition ratio for the object of interest 7. That final composition ratio may be displayed on a display unit 40 of the device 3. Furthermore, the device 3 may provide the object type of the object of interest 7 via an output unit 31.

The tumor malignancy assessment scheme module 6 may receive the object type and perform an assessment about the malignancy of the object of interest.

The device 3 may further be connected to a computer readable device 4 comprising a computer program element 5 which is adapted to control the device 3 such that the device 3 performs the method being described above.

Figure 2:
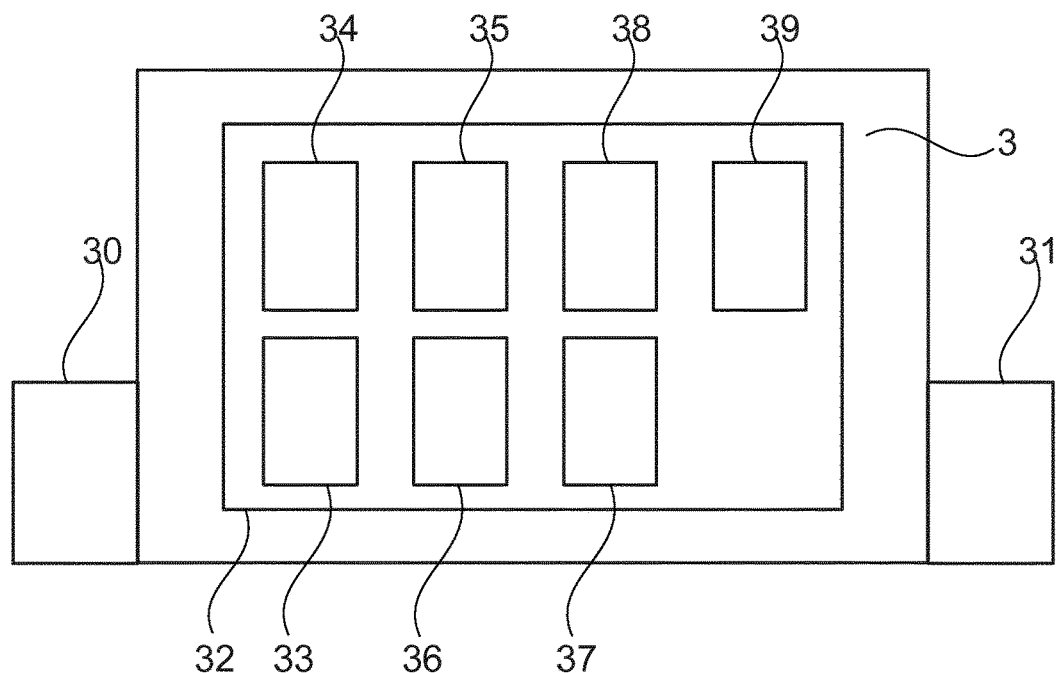
FIG. 2 shows a schematic view of the device for modeling a composition of an object of interest.

For performing the method mentioned above, the device 3 comprises a processing unit 32 being shown in FIG. 2.

The processing unit 32 comprises an image data segmenter 33, and extraction module 34, a sorting module 35, a definition module 36, an assigning module 37, a comparator 38, and a folding module 39.

The image data segmenter 33 segments the object of interest image data into a plurality of image segments 71-80. The image segments 71-80 may be voxels or pixels depicting portions of the object of interest 7. The segmentation may be represented by a label volume or by a surface mesh.

The extraction module 34 extracts the determined Hounsfield density value of each image segment 71-80. The determined Hounsfield densities represent the absorption of the object of interest 7 being determined by the computer tomography calculation. The Hounsfield density value may be represented by a grayscale value of the object of interest image data.

FIG. 6a shows a schematic view of the image segments 71-80, wherein the horizontal lines in the squares represents the determined Hounsfield density values.

The sorting module 35 sorts the image segments 71-80 based on the determined Hounsfield density value. This means, the sorting module 35 generates a sorted list 81 which comprises the image segments 71-80 wherein the determined Hounsfield density value of each image segment 71-80 determines the rank of the sorted list 81.

An example of a sorted list 81 is shown in FIG. 6b. If the sorted list 81 is for example a linear list having two end portions, one end portion comprises the image segments 71-80 having the highest determined Hounsfield density values whereas the other end portion comprises the image segments 71-80 having the lowest determined Hounsfield density values.

The definition module 36 defines a component ratio of component classes 91 to 94 for the object of interest 7. For example, it is assumed that the object of interest 7 comprises four component classes 91 to 94. If the object of interest 7 is a nodule, the component class 91 may represent calcified tissue having an assumed calcified Hounsfield density value of 300 as component Hounsfield density value, the component class 92 may represent solid tissue having an assumed solid Hounsfield density value of 0 as component Hounsfield density value, the component class 93 may represent ground-glass tissue having an assumed ground-glass Hounsfield density value of −500 as component Hounsfield density value, and the component class 94 may represent parenchyma having an assumed parenchyma Hounsfield density value of −750 to −950 as component Hounsfield density value. FIG. 6c shows a schematic view of the component classes 91 to 94, wherein the dot in the squares represents the determined Hounsfield density value.

The component ratio of the component classes 91 to 94 may be assumed to be 40%:20%:20%:20% as the ratio between component class 91 versus component class 92 versus component class 93 versus component class 94. The portions of the component classes 91 to 94 may sum up to 100%.

The assigning module 37 assigns at least one component class 91 to 94 to each image segment 71-80 based on the determined Hounsfield density value from that image segment 71-80. Since in this example, the image segments 71-80 are sorted in a sorted list 81, the first 40% of image segments 71-80 of the sorted list 81 are assigned the component Hounsfield density value of the component class 91, i.e. the component Hounsfield density value of 300. According to FIG. 6d, the first 40% of the sorted list 81 are image segments 78, 79, 72, and 76 which are assigned the component class 91. The rest of the image segments 71-80 is assigned accordingly, i.e. the following 20% of the sorted list 81, being image segments 74 and 80, are assigned component class 92, the next 20% of the sorted list 81, being image segments 77 and 73, are assigned component class 93, and the last 20% of the sorted list 81, being image segments 71 and 75, are assigned the component class 94.

The processing unit creates simulated image data by generating simulated image segments being at the same position in the simulated image data as the image segments 71-80 in the object of interest image data. The simulated image segments comprise the respective component Hounsfield density values being determined by the assigning module 37.

The folding module 39 may simulate a blurring by mathematically folding 106 a blurring function with the simulated image data. The blurring function may be a Gaussian having the width B. Further, the blurring function may simulate the point distribution function of a computer tomography scanner.

In an alternative embodiment, the folding module 39 may simulate blurring by mathematically folding a known device blurring function with the simulated image data. The known device blurring function exactly simulates the blurring of a specific device being used for acquiring the computer tomography data.

The comparator 38 determines the deviation between the simulated image data and the object of interest image data. Further, the comparator may use a distance measure to determine the deviation between the simulated image data and the object of interest image data. The distance measure may be for example the mean difference or a linear correlation. If the comparator determines that the deviation is above a predefines minimum deviation, the processing unit 32 repeatedly runs the definition module 36, the assigning module 37, the comparator 38, and the folding module 39 wherein the definition module 36 amends the component ratio in each iteration. A further iteration may therefore be performed with a component ratio of 35%:25%:20%:20%.

By only amending the component ratio, a big amount of computing time may be saved compared to known simulation methods. The optimization of the function of the component ratio and the blurring function can be performed using a standard-optimizer algorithm, or by exhaustive parallel search, as the required computation cost per trial is very small. After the amendment of the component ratio the assignment of the component Hounsfield density values follows a well-defined assignment scheme which may be performed in a short time. The method described above ensures that the determined Hounsfield density values of the image segments 71-80 are taken into account when trying to find the final composition ratio of the object of interest. Therefore, a randomly performed trial and error approach is prevented.

If the comparator 38 determines that the deviation between the simulated image data and the object of interest image data corresponds to a predefined minimum deviation, i.e. if the deviation equals the predefined minimum deviation or is below the predefined minimum deviation, the component ratio of the last iteration is defined to be the final component ratio. The device 3 may further comprise a storage unit (not shown) being configured to store information about a predefined minimum deviation.

Before the definition module 36 defines a component ratio, a Hounsfield density value of the area surrounding the object of interest 7 may be determined as a peak of the Hounsfield histogram in a certain neighborhood around the object of interest 7, e.g. around a 40 mm radius.

Further, in order to provide optimized comparisons conditions, all image data 9 outside the object of interest image data in the computer tomography image 8 data may be set to the parenchyma Hounsfield density value. The image data 9 outside of the object of interest image data is then uniform.

Furthermore, the simulated tissue being outside the object of interest 7 in the simulated image data may also be set to the parenchyma Hounsfield density value such that the comparison only finds deviations between the simulated image data and the object of interest image data.

Figure 4:
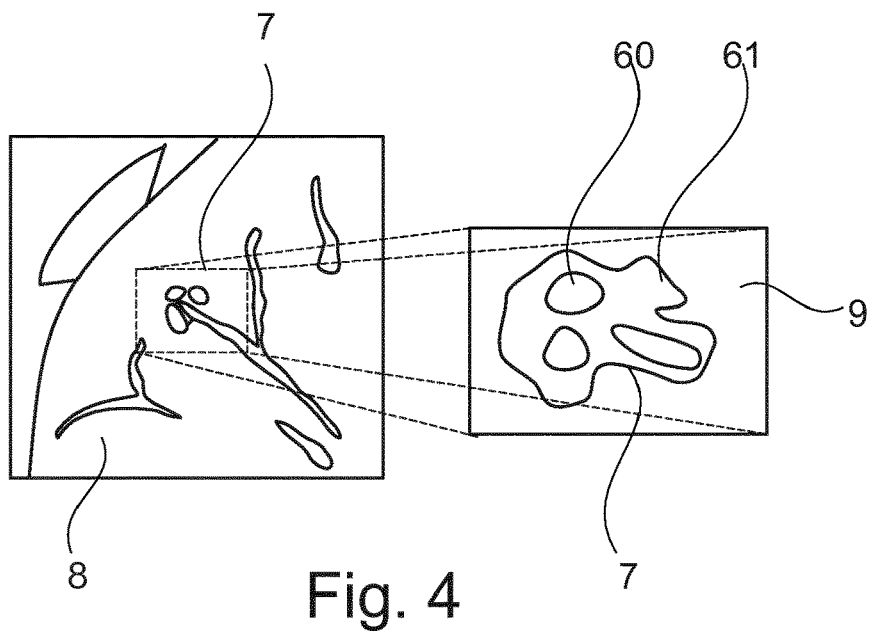
FIG. 4 shows schematic computed tomography image data comprising a nodule as an object of interest.

In FIG. 4, schematic computer tomography image data 8 comprising object of interest image data depicting an object of interest 7 is shown. Furthermore, a zoom shows an enlargement of the object of interest image data and some tissue image data 9 surrounding the object of interest data. In the zoomed image, the tissue image data 9 is set to a uniform Hounsfield density value. This provides a uniform contrast to the object of interest image data.

Figure 7:
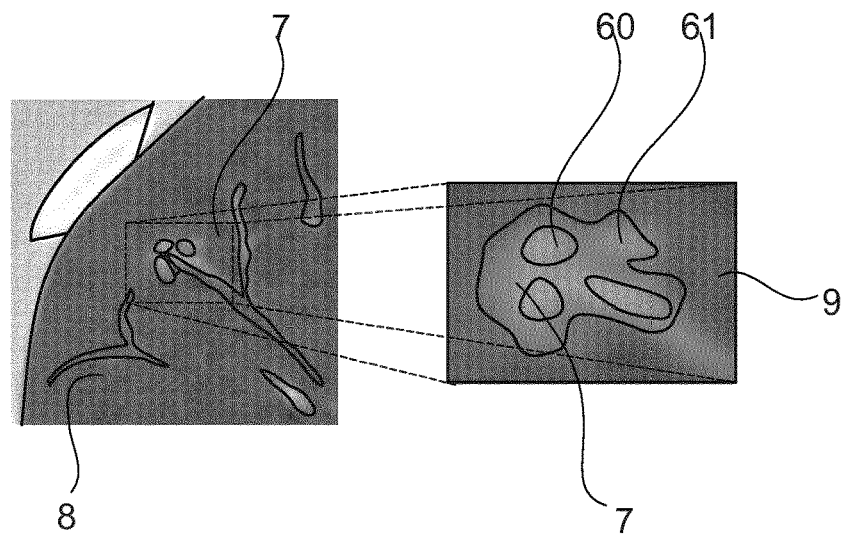
FIG. 7 shows exemplary computed tomography image data of FIG. 4 comprising a nodule as an object of interest.

The object of interest image data comprises bright regions 60 having a high determined Hounsfield density value and dark regions 61 having a low determined Hounsfield density value. The bright regions 60 may have a continuous transition region to the dark regions 61. However, in FIG. 4 the borders of the bright regions 60 are shown as clear borders to clearly distinguish between the right and dark regions 60, 61. The original computer tomography image data 8 comprising the object of interest 7 is shown in FIG. 7.

Figure 5:
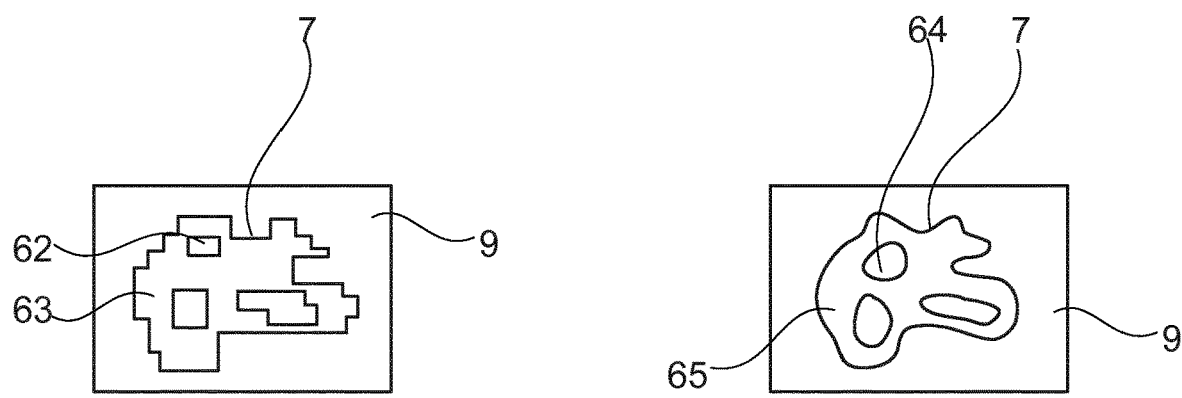
FIG. 5 shows a comparison between schematic simulated image data and schematic determined object of interest data.

FIG. 5 shows three schematic simulated image data a), b), and c). FIG. 5d) shows the object of interest image data being extracted from FIG. 4. Thereby, FIG. 5a) shows a simulation with a width B of 0 mm, b) shows a simulation with a width B of 0.5 mm, c) shows a simulation with the width B of 0.7 mm.

FIGS. 5a) and 5c) show a significant deviation between the object of interest image data in FIG. 5d). In FIG. 5a), a bright region 62 comprises sharp borders to a dark regions 63 since the blurring function having a width B of 0 mm does not provide a significant blurring effect of the bright and dark regions 62, 63. FIG. 5c) shows bright regions 66 which are only slightly brighter than the dark regions 67. The transition between the bright region 66 and the dark regions 67 seems to be smooth. The blurring function having a width B of 0.7 mm provides too much blurring when compared to FIG. 5d) comprising the object of interest image data. The bright region 64 is more blurred than the bright region 62 of FIG. 5a) but less blurred than the bright region 66 of FIG. 5c).

FIG. 5b) shows simulated image data having a very small deviation when compared to the object of interest image data in FIG. 5d). In that example, the composition ratio as well as the width of the blurring function of FIG. 5b) may be chosen as final composition ratio.

Figure 8:
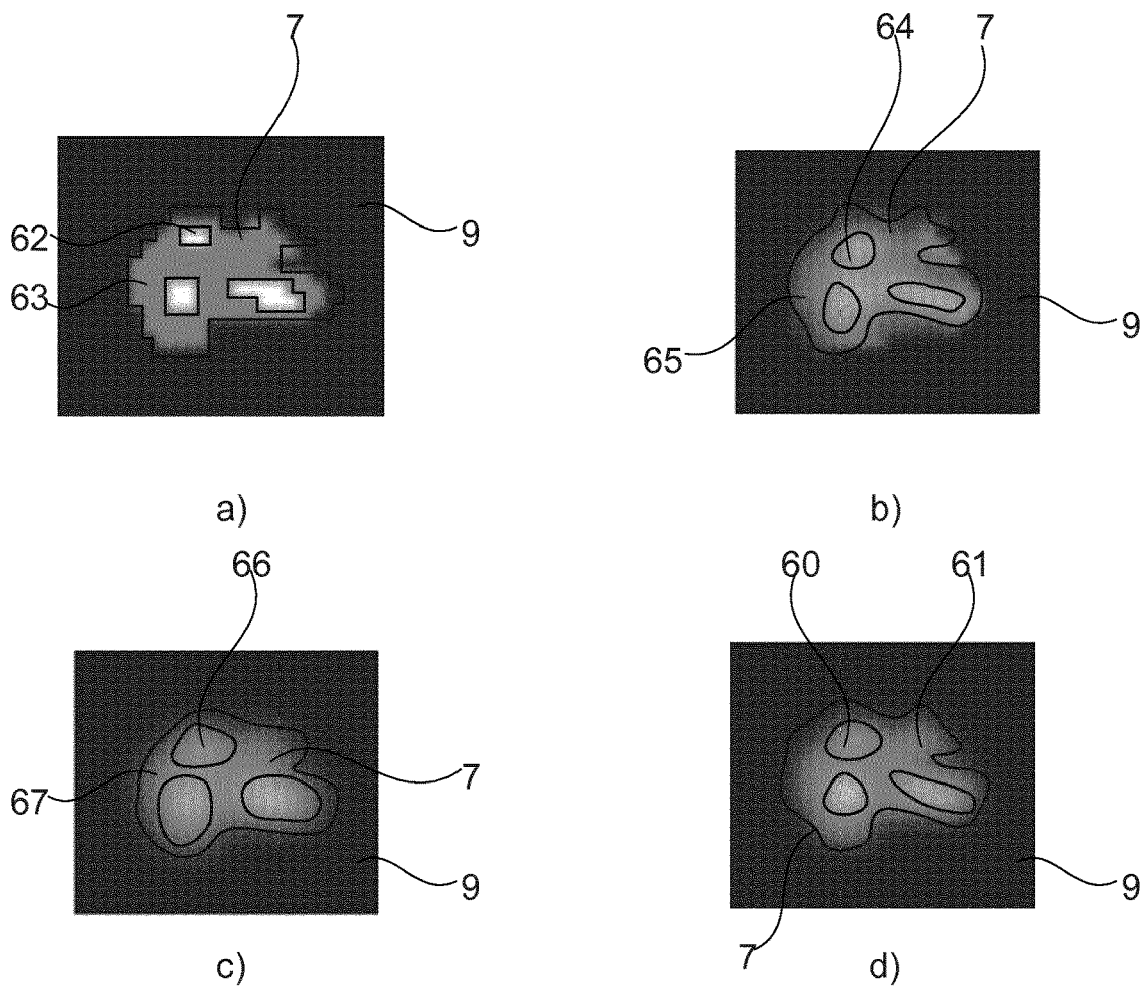
FIG. 8 shows a comparison of FIG. 5 between simulated image data and the determined object of interest data of FIG. 7.

FIG. 8 shows the original simulated image data which are shown as schematic drawings in FIG. 5.

The final component ratio may be compared with a predefined object type list. The predefined object type list may be a textbook-like rule to find an object type of the object of interest. The rules for determining the object type may e.g. be calcified if the final component ratio determines more than 50% for component class 91, solid if the final component ratio determines more than 50% for component class 92, mixed if the final component ratio determines more than 50% for component class 93 and more than 5% for component class 92, and ground-glass otherwise. In case, the object of interest is a nodule the final component ratio may determine what kind of nodule has been simulated.

The determined object type may be communicated to a user by the display unit 40. The user can then decide how to further use that result.

Furthermore, the tumor malignancy assessment scheme 6 may receive the determined object type. That assessment scheme 6 may provide criteria which may provide boundaries for different tumor types and their malignancy potential. The outcome of the tumor malignancy assessment scheme 6 may be provided to a user.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for modelling a composition of an object of interest, the device comprising:
at least one processor configured to:
segment the object of interest image data provided by computer tomography image data into image segments;
extract a Hounsfield density value from the image segments;
define a component ratio of at least two component classes for the object of interest, the at least two component classes having different component Hounsfield density values;
assign at least one component class to each image segment based on the corresponding determined Hounsfield density value resulting in simulated image segments comprising the component Hounsfield density values, the simulated image segments defining simulated image data of the object of interest, wherein a ratio of the assigned component classes corresponds to the component ratio;
determine a deviation between the simulated image data and the object of interest image data; and
vary the component ratio until the deviation corresponds to a predefined minimum deviation resulting in a final component ratio.

2. The device according to claim 1, wherein the at least one processor is configured to sort the image segments based on the determined Hounsfield density values resulting in a sorted list of image segments; and
to segment the sorted list into portions, the ratio between the portions being the component ratio, and wherein the component classes are assigned to the portions of the sorted list in accordance with the component ratio.

3. The device according to claim 1, wherein the at least one processor is configured to fold the simulated image data with a blurring function; and
to vary the blurring function when varying the component ratio.

4. The device according to claim 1, further comprising a display;
wherein the at least one processor is further configured to compare the final component ratio with a predefined object type list resulting in a determined object type of the object of interest; and
wherein the display is configured to communicate the determined object type to a user.

5. The device according to claim 4, further comprising: an output;
wherein the object of interest is a tumor; and
wherein the output is configured to transmit the determined object type into a tumor malignancy assessment scheme.

6. A system for modelling a composition of an object of interest, comprising:
a computer tomography imaging device; and
a device comprising:
at least one processor configured to:
segment the object of interest image data provided by computer tomography image data into image segments;
extract a Hounsfield density value from the image segments;
define a component ratio of at least two component classes for the object of interest, the at least two component classes having different component Hounsfield density values;
assign at least one component class to each image segment based on the corresponding determined Hounsfield density value resulting in simulated image segments comprising the component Hounsfield density values, the simulated image segments defining simulated image data of the object of interest, wherein a ratio of the assigned component classes corresponds to the component ratio;
determine a deviation between the simulated image data and the object of interest image data; and
vary the component ratio until the deviation corresponds to a predefined minimum deviation resulting in a final component ratio.

7. A method for modelling a composition of an object of interest, the method comprising:
segmenting object of interest image data provided by computer tomography image data resulting in a plurality of image segments;
extracting a determined Hounsfield density value from the object of interest image data for each image segment;
defining a component ratio of at least two component classes for the object of interest, the at least two component classes having different component Hounsfield density values;
assigning at least one component class to each image segment based on the corresponding determined Hounsfield density value resulting in simulated image segments comprising the component Hounsfield density values, the simulated image segments defining simulated image data of the object of interest, wherein a ratio of the assigned component classes corresponds to the component ratio;
determining a deviation between the simulated image data and the object of interest image data; and
varying the component ratio until the deviation corresponds to a predefined minimum deviation resulting in a final component ratio.

8. The method according to claim 7, further comprising:
sorting the image segments based on the determined Hounsfield density values resulting in a sorted list of image segments; and
segmenting the sorted list into portions, the ratio between the portions corresponding to the component ratio, and wherein the component classes are assigned to the portions of the sorted list in accordance with the component ratio.

9. The method according to claim 7, further comprising:
folding the simulated image data with a blurring function; wherein the blurring function is varied when varying the component ratio.

10. The method according to claim 7, further comprising:
comparing the final component ratio with a predefined object type list resulting in a determined object type of the object of interest; and
communicating the determined object type to a user.

11. The method according to claim 10, wherein the object of interest is a tumor; and wherein the method further comprises: feeding the determined object type into a tumor malignancy assessment scheme.

12. A non-transitory computer-readable medium having one or more executable instructions stored thereon which, when executed by at least one processor, cause the at least one processor to perform a method for modelling a composition of an object of interest, the method comprising:

segmenting object of interest image data provided by computer tomography image data resulting in a plurality of image segments;

extracting a determined Hounsfield density value from the object of interest image data for each image segment;

defining a component ratio of at least two component classes for the object of interest, the at least two component classes having different component Hounsfield density values;

assigning at least one component class to each image segment based on the corresponding determined Hounsfield density value resulting in simulated image segments comprising the component Hounsfield density values, the simulated image segments defining simulated image data of the object of interest, wherein a ratio of the assigned component classes corresponds to the component ratio;

determining a deviation between the simulated image data and the object of interest image data; and varying the component ratio until the deviation corresponds to a predefined minimum deviation resulting in a final component ratio.

* * * * *